United States Patent
Röhl et al.

(10) Patent No.: US 8,156,828 B2
(45) Date of Patent: Apr. 17, 2012

(54) SAMPLING OF INDIVIDUAL ROD-LIKE ARTICLES OF THE TOBACCO-PROCESSING INDUSTRY FROM A MASSFLOW

(75) Inventors: Thomas Röhl, Hamburg (DE); Jürgen Schmid-Dörnte, Ostbevern (DE)

(73) Assignee: Hauni Maschinenbau AG, Hamburg (DE)

( * ) Notice: Subject to any disclaimer, the term of this patent is extended or adjusted under 35 U.S.C. 154(b) by 604 days.

(21) Appl. No.: 12/358,402

(22) Filed: Jan. 23, 2009

(65) Prior Publication Data

US 2009/0193912 A1    Aug. 6, 2009

(30) Foreign Application Priority Data

Jan. 24, 2008   (DE) .................... 10 2008 005 964

(51) Int. Cl.
*G01N 1/20* (2006.01)
(52) U.S. Cl. ..................................... 73/863.91
(58) Field of Classification Search .................. None
See application file for complete search history.

(56) References Cited

U.S. PATENT DOCUMENTS

| | | | |
|---|---|---|---|
| 2,256,598 A | 9/1941 | Ruau | |
| 2,671,551 A | 3/1954 | Fellmann | |
| 4,363,235 A | 12/1982 | Vulliens et al. | |
| 4,882,938 A | 11/1989 | Neri | |
| 4,962,771 A * | 10/1990 | Neri et al. | 131/282 |
| 4,969,551 A * | 11/1990 | Heitmann et al. | 198/384 |
| 5,150,621 A | 9/1992 | Moore et al. | |
| 5,209,127 A * | 5/1993 | Milliner et al. | 73/863.91 |
| 5,214,969 A * | 6/1993 | Adkins et al. | 73/866 |
| 6,968,750 B2 * | 11/2005 | Wilson | 73/863.51 |
| 2003/0167860 A1 | 9/2003 | Wilson | |

FOREIGN PATENT DOCUMENTS

| | | |
|---|---|---|
| DE | 38 12 039 | 10/1988 |
| EP | 0 500 302 | 8/1992 |
| GB | 2 068 870 | 8/1981 |
| GB | 2 203 626 | 1/1988 |
| LU | 43 222 | 9/1992 |
| WO | 01/93706 | 12/2001 |

* cited by examiner

*Primary Examiner* — Robert R Raevis
(74) *Attorney, Agent, or Firm* — Greenblum & Bernstein, P.L.C.

(57) ABSTRACT

Method for sampling individual rod-like articles of the tobacco-processing industry from an article massflow via a sampling unit. The article massflow includes a plurality of rod-like articles arranged longitudinally and axially parallel to each other and is conveyed along a conveying section at a predetermined conveyor speed. The method includes moving the sampling unit parallel to a conveyor direction of the article massflow, capturing at least one individual rod-like article from the article massflow with the sampling unit, and removing the captured at least one individual rod-like article from the article massflow in a direction at an angle to the conveyor direction of the article massflow.

15 Claims, 1 Drawing Sheet

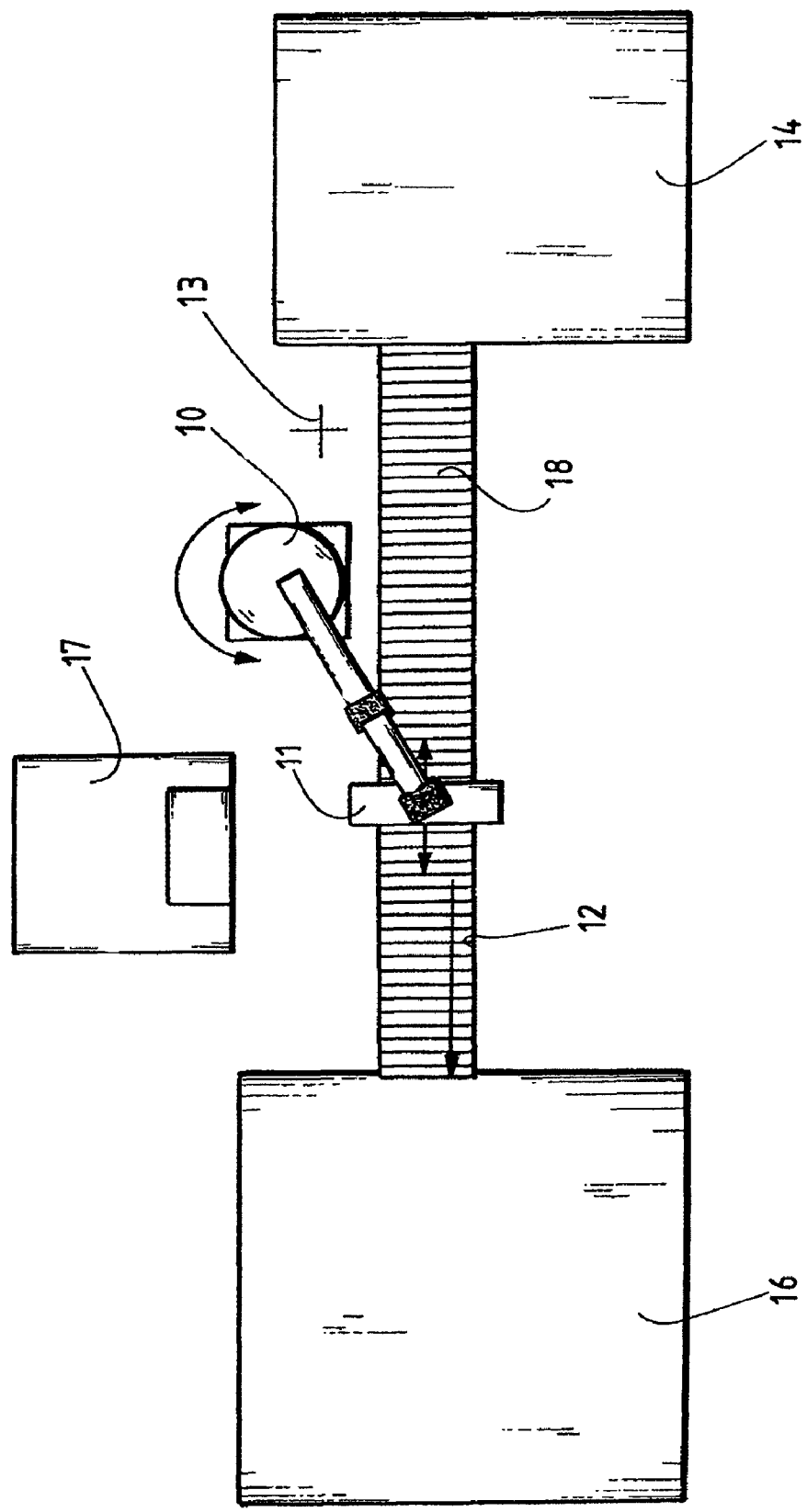

SAMPLING OF INDIVIDUAL ROD-LIKE ARTICLES OF THE TOBACCO-PROCESSING INDUSTRY FROM A MASSFLOW

CROSS-REFERENCE TO RELATED APPLICATIONS

The present application claims priority under 35 U.S.C. §119 of German Patent Application No. 10 2008 005 964.1 filed Jan. 24, 2008, the disclosure of which is expressly incorporated by reference herein in its entirety.

BACKGROUND OF THE INVENTION

1. Field of the Invention

Embodiments of the invention relate to a method for sampling individual rod-like articles of the tobacco-processing industry, in particular filter cigarettes, from an article massflow via a sampling unit. The articles in the article massflow are arranged longitudinally and axially parallel to each other and the article massflow is conveyed along a linear, preferably horizontal, conveying section with a predetermined conveyor speed, preferably continuously. Moreover, embodiments of the invention relate to performing the method with a multi axis robot.

2. Discussion of Background Information

After the manufacturing of filter cigarettes, e.g., on a filter tipping machine, the completed filter cigarettes are conveyed in a massflow, in which filter cigarettes are stacked on top each other, on a conveyor to a cigarette reservoir or to a finishing machine, e.g., a packing machine. In order to monitor the production of the filter cigarettes and to perform a quality control, individual filter cigarettes from the production line can be removed at set time intervals in order to check them in a separate testing station with respect to dimensions of the material and/or other relevant criteria. To achieve this, individual filter cigarettes are removed from the tightly packed massflow with filter cigarettes. This sampling of test cigarettes from the massflow can be executed manually by the operating personnel. Moreover, a sampling unit for withdrawing test cigarettes from the article massflow is known from German Patent Application No. DE 38 12 039 A1.

SUMMARY OF THE INVENTION

Starting from the above-discussed state of the art, embodiments of the present invention improve the automatic sampling of individual rod-like articles from a tightly packed article massflow. The random sampling of articles according to the embodiments is intended to be as gentle as possible and, in particular, the automatic sampling of articles is intended to not disturb the movement of the article flow.

According to embodiments of the invention, a method for sampling individual rod-like articles of the tobacco-processing industry, such as filter cigarettes, from an article massflow with a sampling unit is provided. The article massflow with the articles arranged longitudinally and axially parallel to each other in the article massflow are conveyed along a linear, preferably horizontal, conveying section with a predetermined conveyor speed, preferably continuously. Moreover, during the sampling of articles, the sampling unit moves parallel to the article massflow, preferably at the same conveyor speed of the article massflow, and individual rod-like articles are captured alone or in an article package with several articles from the article massflow by the sampling unit. The captured articles are then removed from the article massflow in a direction diagonal to the conveyor direction, preferably in a direction perpendicular to the conveyor direction of the article massflow via the sampling unit.

Embodiments of the invention are include a sampling unit that executes a movement parallel to the linear movement of the article massflow, and that captures individual articles from the article massflow during the parallel linear movement of the sampling unit and subsequently gently removes them from the article flow. Thus, in accordance with embodiments of the invention, the sampling unit follows the article massflow.

Within the framework of the embodiments of the invention, article massflow is understood as a massflow of rod-like articles stacked one above the other as well as next to each other. In a linear conveying section, the longitudinal axes of the rod-like articles are aligned parallel to each other in a tightly stacked package of the massflow. The individual articles in the article massflow are preferably conveyed linearly in a transverse and axial direction, i.e., perpendicular to their longitudinal alignment or extent, on a conveyor, e.g., belt conveyor or suchlike. The height of an article massflow is typically a multiple of the diameter of each individual filter cigarette or a rod-like article.

Based on the parallel movement of the sampling unit with respect to the conveyor direction of the article massflow, the articles to be removed can be gently removed from the article massflow. In this way, the longitudinal and axial alignment of the articles to be removed and the articles remaining in the massflow experiences no change during the sampling process. In relation to the moving massflow, the article to be removed is moved in the longitudinal and axial direction or is removed in a non-parallel direction to the conveyor direction of the article massflow. Further, the article to be removed can be moved, e.g., upwards with respect to the moving article massflow.

In the present context, when the sampling of individual articles or filter cigarettes is discussed, it should also be understood within the framework of the embodiments of the invention that rod-like articles can be removed alone or in an article package. The number of removed cigarettes or rod-like articles is very small compared to the number articles in the article massflow.

It is thus provided in a further embodiment of the method that the articles are removed from the preferably horizontally moving article massflow by a transverse movement of the sampling unit relative to the conveyor direction of the article massflow while also moving the sampling unit parallel to the conveyor direction of the article massflow. Due to the fact that the sampling unit generally follows the linear movement of the massflow for a predetermined time period or a predetermined conveying section during the sampling process, the position or alignment of the articles of the massflow remaining after the sampling process is not disturbed due to the compact arrangement.

Moreover, in a further embodiment of the method, the articles are removed from the preferably horizontal and continuously conveyed article massflow in a direction transverse and axial upwards or longitudinally and axially laterally.

In order to check a sample of, e.g., manufactured filter cigarettes, embodiments of the method include that the rod-like articles removed from the article massflow are transferred to an inspection unit in order to test the quality of the removed articles with respect to quality-relevant parameters, such as diameter, weight, etc.

The article massflow is preferably conveyed between an article manufacturing machine, e.g., a filter tipping machine, and either an article finishing machine or an article reservoir, or between the article reservoir and the article finishing machine. The article massflow may preferably be conveyed in a conveying section of a conveyor or in a viewing section horizontally. A simple sampling of test cigarettes can be achieved after the manufacturing process on a filter assembler machine. In the way, the manufactured filter cigarettes can be conveyed in a massflow to a cigarette reservoir or, e.g., to a packer.

A simplified handling during the sampling of the articles results in the articles being removed from the article massflow by a sampling unit on an arm of a multi axis robot with at least four, and preferably five or six, degrees of freedom of movement. Through the use of the multi axis robot, a simple and fast-reaction sampling unit is provided in combination with the sampling unit arranged on the arm of the multi axis robot. High position accuracy of the pick-up device is achieved on an article flow in order to remove in a targeted manner individual filter cigarettes or rod-like articles from the massflow. Through the use of the multi axis robot with at least four degrees of freedom of movement, it is ensured that the sampling unit can be conveyed or follows parallel to the conveyor device of the massflow. The degrees of freedom of movement of the multi axis robot are understood as movement axes, around which the corresponding movement elements, e.g., arms or suchlike, can be moved or pivoted.

The multi axis robots discussed within the context of the embodiments of the invention are understood to be controllable or self-learning, i.e., multi axis robots equipped with a neuronal network, which can independently correct the positions based on the neuronal network. In this manner, a high level of precision may be achieved in the execution of movements.

Moreover, according to an embodiment of the method, the multi axis robot can be arranged as a robot, preferably as a mobile and non-stationary robot, on the conveying section of a preferably linearly conveying conveyor for a predetermined period of time. As the multi axis robot is not necessarily designed or arranged permanently or fixed on a conveying section, it is possible to move the multi axis robot after sampling at a first conveying section or at the first conveying section of a production line to another conveying section of a second production line in order to perform corresponding samplings of articles from the second production line from an article massflow. Through use of a mobile and movable, i.e., non-stationary, multi axis robot, a high level of flexibility may be achieved during the sampling from several conveying sections, since the multi axis robot with the sampling unit can be used one after the other for several massflows. In this manner, different product flows can be easily monitored in close-mesh manner.

Moreover, the use of a multi axis robot for different massflows in several product lines considerably decreases the cost of product monitoring or quality control of filter cigarettes, whereby a particularly effective setup and arrangement of a sampling system results. The multi axis robot can thereby alternately remove articles from several simultaneously running article massflows and guide them to a common inspection system or a common inspection unit.

In one embodiment, the inspection unit or measuring device can thereby be arranged in a movable manner for the articles removed from the massflows so that the inspection unit and the robot do not need to be permanently located at the production machines or the conveyor devices.

Furthermore, it may be advantageous if the multi axis robot receives corresponding movement control commands for the control of the movement guidance of the sampling unit arranged on one arm end when the multi axis robot is arranged on one conveying section using a reference point for this conveying section. Through the individual, machine-specific reference point on a production line or on a machine and on a conveyor device, the multi axis robot can be geometrically calibrated using the reference point. The machine-specific characteristics are communicated to the multi axis robot, e.g., by a barcode or another identification object. The data transfer of the movement control commands can thereby also take place by a data connection (which can be wireless) to the multi axis robot.

In particular, after receipt of the movement control commands, the sampling unit can be aligned with the article massflow and/or approach the article massflow based on predetermined or defined algorithms in a contour-controlled manner to the article massflow and can be conveyed parallel to the article massflow.

After the alignment and approach of the sampling unit, an embodiment of the invention provides that one or more articles to be removed can be detected in the article massflow by a detection device on the sampling unit and these may then be picked up by the sampling unit.

The withdrawing of the articles from the massflow can take place, e.g., through a suctioning from above by a lifting mechanism. Moreover, it is possible in an embodiment to remove the articles to be removed from the side, preferably on the filter side of filter cigarettes, by suctioning of one or more cigarettes from the moving article massflow. Moreover, it is possible in another embodiment that during the sampling the sampling unit reaches into the material flow with a tactile gripper and lifts an article or package out of the massflow. During the sampling of the rod-like articles from the massflow, the sampling unit is hereby designed synchronously with the conveyor movement of the article flow, so that the articles are removed from the conveyed article flow without changing or disturbing the remaining material flow in the article flow or the position and alignment of the articles remaining in the massflow. The robot or the sampling unit of the robot can synchronously follow the transport speed of the massflow.

Moreover, the method includes that the articles are removed from the article massflow by a sampling unit designed as a gripper or with a suction device.

Embodiments of the invention utilize a multi axis robot for the sampling of individual rod-like articles of the tobacco-processing industry, in particular filter cigarettes, from an article massflow. The method for the sampling of individual rod-like articles can be executed in the above-described manner. We expressly refer to the above explanations in order to avoid repetitions.

Embodiments of the invention are directed to a method for sampling individual rod-like articles of the tobacco-processing industry from an article massflow via a sampling unit. The article massflow includes a plurality of rod-like articles arranged longitudinally and axially parallel to each other and is conveyed along a conveying section at a predetermined conveyor speed. The method includes moving the sampling unit parallel to a conveyor direction of the article massflow, capturing at least one individual rod-like article from the article massflow with the sampling unit, and removing the captured at least one individual rod-like article from the article massflow in a direction at an angle to the conveyor direction of the article massflow.

According to aspects of the invention, the individual rod-like articles can be filter cigarettes, the conveying section can be linear and horizontal, and the article massflow can be continuously conveyed.

According to other aspects of the invention, the sampling unit may be moved at a same speed as the conveyor speed of the article massflow.

In accordance with still other aspects of the invention, the captured at least one individual rod-like article may be an article package with several articles.

In accordance with other aspects of the present invention, the angle to the conveyor direction of the article massflow can be perpendicular to the conveyor direction of the article massflow.

Moreover, the captured at least one individual rod-like article may be removed from the article massflow by movement of the sampling unit in a direction transverse to the conveyor direction of the article massflow along with movement of the sampling unit in a direction parallel to the conveyor direction of the article massflow. The captured at least one individual rod-like article may be removed from the article massflow in at least one of a transversely and axially upwardly direction and a longitudinally and axially laterally direction.

According to aspects of the instant invention, the removed at least one individual rod-like article can be transferred to an inspection unit.

In accordance with other aspects of the invention, the article massflow may be conveyed between an article manufacturing machine and one of an article finishing machine or an article reservoir. The article manufacturing machine can be a filter tipping machine.

According to still other aspects of the invention, the article massflow can be conveyed between an article reservoir and an article finishing machine.

The sampling unit may be arranged on an arm of a multi axis robot with at least four, and preferably five or six, degrees of freedom of movement. The multi axis robot may be arranged on the conveying section for a predetermined period of time. The multi axis robot is a mobile and non-stationary robot. Further, the multi axis robot can receive movement control commands for controlling guidance and movement of the sampling unit when the multi axis robot is arranged on a reference point for the conveying section. Also, after receipt of the movement control commands, the sampling unit at least one of is aligned with the article massflow and approaches the article massflow, and is conveyed parallel to the article massflow.

In accordance with still yet other aspects of the present invention, the sampling unit can include at least one of a gripper and a suctioning device.

Embodiments of the invention are directed to a method to sample individual rod-like articles of the tobacco-processing industry from an article massflow with a multi axis robot. The article massflow includes a plurality of rod-like articles arranged longitudinally and axially parallel to each other and being conveyed along a conveying section at a predetermined conveyor speed, and the method includes moving a sampling unit coupled to an arm of the multi axis robot parallel to a conveyor direction of the article massflow, capturing at least one individual rod-like article from the article massflow with the sampling unit, and removing the captured at least one individual rod-like article from the article massflow in a direction at an angle to the conveyor direction of the article massflow.

Other exemplary embodiments and advantages of the present invention may be ascertained by reviewing the present disclosure and the accompanying drawing.

BRIEF DESCRIPTION OF THE DRAWINGS

The present invention is further described in the detailed description which follows, in reference to the noted drawing by way of non-limiting example of an exemplary embodiment of the present invention, wherein:

The Figure illustrates a top view of an arrangement for a robot at a conveying section according to the invention

DETAILED DESCRIPTION OF THE PRESENT INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

The Figure illustrates a top view of an arrangement according to the invention of a mobile multi axis robot 10 at a viewing section or horizontal conveying section 12. Linear conveying section 12 is located between a filter tipping machine 14 and a transfer device 16 (e.g., a rod transfer system (RTS)), which conveys a massflow of the filter cigarettes produced on filter assembler machine 14 into a downstream reservoir (e.g., flexible mass follow reservoir (FMR)). Conveying section 12, which is preferably horizontally designed or oriented, is arranged to convey a tightly packed massflow 18 with filter cigarettes that are arranged to be tightly stacked one above the other and next to each other in a transverse and axial direction (relative to the individual articles of the massflow) to the transfer device.

In tightly packed massflow 18, the filter cigarettes are aligned longitudinally and axially with respect to each other, such that several layers of articles or filter cigarettes are arranged on top of each other in massflow 18.

Multi axis robot 10 has several arms or movement elements that can each be moved around corresponding axes. The multi axis robot preferably has four, five or six degrees of freedom of movement. A gripper 11 is arranged on an end of a movement arm, by which individual filter cigarettes are removed from massflow 18.

In order to remove the filter cigarettes from massflow 18, multi axis robot 10 is moved to a reference point 13 provided on conveying section 12 Multi axis robot 10, which is preferably designed as a self-learning robot, receives corresponding movement control commands or machine-specific or reference data on conveying section 12 in order to preferably reference itself or to perform a geometric calibration so that a corresponding position along conveying section 12 can subsequently be selected and assumed and gripper 11 can be controlled in a contour-controlled manner on massflow 18.

After the approach phase of the gripper 11, the gripper 11 is aligned synchronously and parallel to the massflow 18 according to the conveyor direction of the massflow 18 so that corresponding filter cigarettes in the massflow 18 are detected during this uniform, parallel conveyance of the gripper 11 to the massflow 18 by means of a detector on the gripper 11 and are subsequently captured by the gripper 11.

After the capture of individual filter cigarettes or an article package, gripper 11 moves upwards while retaining the uniform translation movement in the direction of massflow 18 in order to gently remove the captured filter cigarettes from massflow 18. The removed filter cigarettes are then transferred to an inspection unit 17, which is preferably a mobile unit. For the withdrawing of individual filter cigarettes, multi axis robot 10 is provided with a corresponding sensor system and with corresponding, preferably mechanical or pneumatic receivers.

After a performed sampling on conveying section 12, multi axis robot 10 can be moved to another conveying section on another production line in order to remove samples from a second production line. Due to the fact that multi axis robot 10 is designed as a mobile robot, it can also be pushed to other machines or production lines so robot 10 can perform a sampling according to embodiments of the invention of filter cigarettes using a respective reference point on the conveying sections or viewing sections while taking into consideration the spatial conditions at the respective viewing section. The alignment and control of multi axis robot 10 can take place using reference points and a corresponding transmission of specific control data for the respective viewing section.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

List of References
10 Multi axis robot
11 Gripper
12 Conveying section
13 Reference point
14 Filter tipping machine
16 Transfer device
17 Inspection unit
18 Massflow

What is claimed:

1. A method for sampling individual rod-like articles of the tobacco-processing industry from an article massflow via a sampling unit, the article massflow comprising a plurality of rod-like articles arranged longitudinally and axially parallel to each other and being conveyed along a conveying section at a predetermined conveyor speed, the method comprising:
   moving the sampling unit parallel to a conveyor direction of the article massflow;
   capturing at least one individual rod-like article from the article massflow with the sampling unit; and
   removing the captured at least one individual rod-like article from the article massflow in a direction at an angle to the conveyor direction of the article massflow,
   wherein the sampling unit is arranged on an arm of a multi axis robot with at least four degrees of freedom of movement.

2. The method in accordance with claim 1, wherein the individual rod-like articles are filter cigarettes, the conveying section is linear and horizontal, and the article massflow is continuously conveyed.

3. The method in accordance with claim 1, wherein the sampling unit is moved at a same speed as the conveyor speed of the article massflow.

4. The method in accordance with claim 1, wherein the captured at least one individual rod-like article is removed from the article massflow by movement of the sampling unit in a direction transverse to the conveyor direction of the article massflow along with movement of the sampling unit in a direction parallel to the conveyor direction of the article massflow.

5. The method in accordance with claim 4, wherein the captured at least one individual rod-like article is removed from the article massflow in at least one of a transversely and axially upwardly direction and a longitudinally and axially laterally direction.

6. The method in accordance with claim 1, wherein the removed at least one individual rod-like article is transferred to an inspection unit.

7. The method in accordance with claim 1, wherein the article massflow is conveyed between an article manufacturing machine and one of an article finishing machine or an article reservoir.

8. The method in accordance with claim 7, wherein the article manufacturing machine is a filter tipping machine.

9. The method in accordance with claim 1, wherein the article massflow is conveyed between an article reservoir and an article finishing machine.

10. The method in accordance with claim 1, wherein the multi axis robot has five degrees of freedom of movement.

11. The method in accordance with claim 1, wherein the multi axis robot has six degrees of freedom of movement.

12. The method in accordance with claim 1, wherein the multi axis robot is arranged on the conveying section for a predetermined period of time.

13. The method in accordance with claim 12, wherein the multi axis robot is a mobile and non-stationary robot.

14. The method in accordance with claim 1, wherein the multi axis robot receives movement control commands for controlling guidance and movement of the sampling unit when the multi axis robot is arranged on a reference point for the conveying section.

15. The method in accordance with claim 1, wherein the sampling unit includes at least one of a gripper and a suctioning device.

* * * * *